United States Patent
Wang et al.

(10) Patent No.: US 10,682,300 B2
(45) Date of Patent: Jun. 16, 2020

(54) AQUEOUS ORAL CARE FLUORIDE TREATMENT COMPOSITIONS, AND METHODS

(71) Applicant: 3M INNOVATIVE PROPERTIES COMPANY, St. Paul, MN (US)

(72) Inventors: Yizhong Wang, Woodbury, MN (US); Tiffany T. Ton, Woodbury, MN (US); Melinda B. Gustafson, Lake Elmo, MN (US); Jennifer Post, St. Paul, MN (US); Paul R. Klaiber, Mahtomedi, MN (US); Carola A. Carrera Vidal, Plymouth, MN (US); Joel D. Oxman, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/148,415

(22) Filed: Oct. 1, 2018

(65) Prior Publication Data
US 2019/0099338 A1 Apr. 4, 2019

Related U.S. Application Data

(60) Provisional application No. 62/565,345, filed on Sep. 29, 2017.

(51) Int. Cl.
| | |
|---|---|
| *A61K 8/21* | (2006.01) |
| *A61K 45/06* | (2006.01) |
| *A61K 33/16* | (2006.01) |
| *A61K 8/73* | (2006.01) |
| *A61K 8/27* | (2006.01) |
| *A61C 19/06* | (2006.01) |
| *A61K 8/19* | (2006.01) |
| *A61K 8/24* | (2006.01) |
| *A61K 8/26* | (2006.01) |
| *A61K 8/81* | (2006.01) |
| *A61Q 11/00* | (2006.01) |

(52) U.S. Cl.
CPC ............ *A61K 8/21* (2013.01); *A61C 19/063* (2013.01); *A61K 8/19* (2013.01); *A61K 8/24* (2013.01); *A61K 8/26* (2013.01); *A61K 8/27* (2013.01); *A61K 8/73* (2013.01); *A61K 8/8147* (2013.01); *A61K 33/16* (2013.01); *A61K 45/06* (2013.01); *A61Q 11/00* (2013.01); *A61K 2800/48* (2013.01); *A61K 2800/5424* (2013.01); *A61K 2800/56* (2013.01)

(58) Field of Classification Search
CPC ............... A61K 8/46; A61K 8/02; A61P 1/02
USPC ........................................................ 424/49
See application file for complete search history.

(56) References Cited

U.S. PATENT DOCUMENTS

| | | | | |
|---|---|---|---|---|
| 4,108,979 A | * | 8/1978 | Muhler | A61K 8/26 424/49 |
| 4,540,576 A | * | 9/1985 | Zahradnik | A61K 8/042 424/52 |
| 5,211,559 A | | 5/1993 | Hart | |
| 5,603,922 A | * | 2/1997 | Winston | A61K 8/19 222/129 |
| 6,582,708 B1 | * | 6/2003 | Sagel | A61K 8/0208 424/401 |
| 8,968,709 B2 | | 3/2015 | Yang | |
| 2004/0115140 A1 | | 6/2004 | Joziak | |
| 2004/0115410 A1 | | 6/2004 | Joziak | |
| 2006/0029908 A1 | * | 2/2006 | Allred | A61C 19/063 433/215 |
| 2007/0122359 A1 | * | 5/2007 | Wang | A61K 8/25 424/52 |
| 2007/0140990 A1 | | 6/2007 | Fetissova | |
| 2016/0220472 A1 | | 8/2016 | Wang | |
| 2016/0220473 A1 | | 8/2016 | Wang | |

FOREIGN PATENT DOCUMENTS

| | | |
|---|---|---|
| WO | WO 2010/068359 | 6/2010 |
| WO | WO 2015/038400 | 3/2015 |

OTHER PUBLICATIONS

Weiss, et al., "The Effect of Iron on in vitro Decalcification of Human Tooth Enamel," Journal of Oral Rehabilitation, 1985, vol. 12, pp. 91-93.
"Topical Fluoride Preparations for Reducing Incidence of Dental Caries," Monograph, Federal Register, May 14, 1974, vol. 39, No. 94.
Mintel, "Mouthwash," Database GNPD, XP055522353, Accession No. 3735681, www.gnpd.com, Jan. 27, 2016.
Mintel, "Antiseptic Mouthwash," Database GNPD, XP055522349, Accession No. 2637699, www.gnpd.comSep. 3, 2014.
International Search Report of International Application No. PCT/IB2018/056752, dated Nov. 9, 2018.

* cited by examiner

*Primary Examiner* — Walter E Webb
(74) *Attorney, Agent, or Firm* — 3M IPC

(57) ABSTRACT

An aqueous oral care fluoride treatment composition, a method of providing fluoride to a patient's tooth surface, and a method of reducing the incidence of dental caries, wherein the composition includes: 0.1 wt-% to 3.0 wt-% of a crosslinked poly acid having carboxylic acid side groups; a pharmaceutically acceptable buffer; 1.0 wt-% to 2.5 wt-% of sodium fluoride; 0.025 wt-% to 1.75 wt-% of a multivalent cation salt; and at least 60 wt-% water; wherein the weight percentages are based on the total weight of the aqueous composition.

22 Claims, No Drawings

AQUEOUS ORAL CARE FLUORIDE TREATMENT COMPOSITIONS, AND METHODS

BACKGROUND

Fluoride treatment involves the application of fluoride to a tooth surface with the formation of fluorapatite and calcium fluoride.

There are two major in-office fluoride treatment methods currently in use. One treatment method uses a fluoride gel/foam in a tray. This method requires several grams of fluoride gel stored in a tray that is then placed into a patient's mouth onto the teeth. This tray is left in the mouth with the gel/foam in contact with the teeth for 1 to 4 minutes. The gel/foam formulation is an aqueous system that includes 2% sodium fluoride. This material requires the use of suction to pull the extra gel out of the mouth to avoid unnecessary high amounts of fluoride ingestion.

Another treatment method is a dental fluoride varnish. Most fluoride varnishes on the market are rosin/ethanol based formulations with a hydrophobic nature. The varnish is painted on the teeth and remains in place for several hours to allow for the fluoride to be released from the composition. Typically, dentists use fluoride varnishes for in-office fluoride treatment. Most dental fluoride varnishes include 5% sodium fluoride. The dose of varnish is about 0.5 gram. Dental varnishes place much smaller amounts of fluoride into a patient's mouth compared to fluoride gel/foams. Thus, fluoride ingestion is less with fluoride varnishes. Also, fluoride varnishes are easier to apply as they are simply painted on a patient's teeth; however, fluoride varnish treatments are more labor intensive than gel treatments and fluoride varnish treatments leave the patient with an unpleasant "dirty teeth" feeling.

Compositions that are as simple to apply to teeth as varnishes and work in time periods as short as gel/foam formulations are desired.

SUMMARY OF THE DISCLOSURE

The present disclosure provides aqueous oral care fluoride treatment compositions and methods of treating (e.g., methods of providing fluoride to a patient's tooth surface).

Such compositions can be used as in-office fluoride treatment compositions. They can be formulated into a composition that can be painted on a tooth surface if desired. They can provide similar fluoride efficacy to that of varnishes in the shorter periods of time of gel/foam formulations.

In one embodiment, the present disclosure provides an aqueous oral care fluoride treatment composition that includes: 0.1 wt-% to 3.0 wt-% of a crosslinked poly acid having carboxylic acid side groups; a pharmaceutically acceptable buffer; 1.0 wt-% to 2.5 wt-% of sodium fluoride; 0.025 wt-% to 1.75 wt-% of a multivalent cation salt; and at least 60 wt-% water; wherein the weight percentages are based on the total weight of the aqueous composition.

In another embodiment, the present disclosure provides a method of providing fluoride to a patient's tooth surface. The method involves applying an aqueous oral care fluoride treatment composition as disclosed herein to the patient's tooth surface.

In another embodiment, the present disclosure provides a method of reducing the incidence of dental caries. The method involves applying an aqueous oral care fluoride treatment composition as disclosed herein to the patient's tooth surface.

As used herein, "alkyl" refers to a monovalent group that is a radical of an alkane and includes straight-chain (i.e., linear), branched, cyclic, and bicyclic alkyl groups, and combinations thereof, including both unsubstituted and substituted alkyl groups. Unless otherwise indicated, the alkyl groups typically contain from 1 to 100 carbon atoms. In some embodiments, the alkyl groups contain 1 to 60 carbon atoms, 1 to 30 carbon atoms, 1 to 10 carbon atoms, 1 to 6 carbon atoms, 1 to 4 carbon atoms, or 1 to 3 carbon atoms. Examples of "alkyl" groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The terms "polymer" and "polymeric material" include, but are not limited to, organic homopolymers, copolymers, such as for example, block, graft, random, and copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The term "room temperature" refers to a temperature of 20° C. to 25° C. or 22° C. to 25° C.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF ILLUSTRATIVE EMBODIMENTS

The present disclosure provides aqueous oral care fluoride treatment compositions. The present disclosure also provides methods of providing fluoride to a patient's tooth surface, as well as methods of reducing the incidence of dental caries. Such methods involve applying an aqueous oral care fluoride treatment composition as described herein to the patient's tooth surface.

In certain embodiments, applying an aqueous oral care fluoride treatment composition includes painting the treatment composition on the patient's tooth surface.

In certain embodiments, applying an aqueous oral care fluoride treatment composition includes dispensing the treatment composition into a dental tray and attaching the tray having the treatment composition therein to the patient's tooth surface. In certain embodiments, the dental tray includes an orthodontic aligner treatment tray.

Aqueous oral care fluoride treatment compositions of the present disclosure include at least 60 wt-%, at least 70 wt-%, or at least 80 wt-%, water, based on the total weight of the aqueous composition. In certain embodiments, a treatment composition includes up to 96 wt-%, or up to 90 wt-%, water, based on the total weight of the aqueous composition.

Treatment compositions of the present disclosure are aqueous compositions. Although they may include a small amount of organic solvent (e.g., (C1-C4) alcohols such as ethanol), preferably they are free of organic solvents that function as liquid carriers (as opposed to organic solvents that are used as carriers/solvents for flavorants or sweeteners). For example, certain additives may be provided as a solution or dispersion in an organic solvent as a liquid carrier. If there is any organic solvent (that functions as a liquid carrier) present in aqueous oral care fluoride treatment compositions of the present disclosure, it is present in an amount of less than 5 wt-%, based on the total weight of the aqueous composition.

Aqueous oral care fluoride treatment compositions of the present disclosure include a pharmaceutically acceptable buffer. The type and amount of such buffer is selected to provide a treatment composition with a pH of at least 6, or at least 6.5. In certain embodiments, the type and amount of such buffer is selected to provide a treatment composition with a pH of up to 8, up to 7.5, or up to 7. In certain embodiments, the type and amount of such buffer is selected to provide a treatment composition with a pH of 6.5 to 7.5, or a pH of 7.0, particularly for methods of reducing the incidence of dental caries, according to the Monograph entitled "Topical Fluoride Preparations for Reducing Incidence of Dental Caries," Federal Register, Vol. 39, No. 94, May 14, 1974.

Poly Acids

Aqueous oral care fluoride treatment compositions of the present disclosure include a crosslinked poly acid. The crosslinked poly acid can be a homopolymer or a copolymer of one or more monomers having one or more carboxylic acid groups.

Examples of monomers having one or more carboxylic acid groups include acrylic acid, maleic acid, maleic anhydride, itaconic acid, vinyl ether, alkyl acrylates, and saccharides. Various combinations of such monomers may be used if desired. In certain embodiments, the crosslinked poly add includes a homopolymer or a copolymer of acrylic acid, maleic acid, itaconic acid, (C10-C30)alkyl acrylate, and a combination thereof. In certain embodiments, the crosslinked poly acid includes a crosslinked polyacrylic acid homopolymer.

Examples of crosslinkers include allyl sucrose, allyl pentaerythritol, glycerol, diglycerol, polyglycerol, polyalkenyl alcohols, or divinyl glycol. Various combinations of crosslinkers may be used if desired. In certain embodiments, the polyacrylic acid is crosslinked with allyl sucrose or allyl pentaerythritol.

Suitable poly acids of the present disclosure assist in providing compositions that can be used to develop semi-solid and liquid formulations with a wide range of flow and rheological properties. The poly acids can also provide one or more of the following functions: highly efficient thickeners; suspending agents; stabilizers that eliminate the problem of settling, even when used at low levels (e.g., 0.1 wt-% to 3.0 wt-%); flow modifiers; and bioadhesion. Preferred poly acids swell when hydrated and neutralized, forming a colloidal dispersion. The insoluble ingredients in the suspensions are then trapped in the interstitial spaces between the hydrogel particles, thereby forming a stable dispersion.

Poly acids may have a wide variety of viscosities. In certain embodiments, the crosslinked poly acid, in a pH 7.5 buffer at 0.5 wt-%, has a viscosity of 4,000-100,000 centipoise (cP).

Exemplary poly acids include linear polyacrylic acids, acrylic acid copolymers, maleic acid/maleic anhydride copolymers, itaconic acid copolymers, vinyl ether and maleic anhydride copolymers such as that available under the tradename GANTREZ (from Ashland), high molecular weight crosslinked polyacrylic acid homopolymers and copolymers such as that available under the tradename CARBOPOL (from Lubrizol Life Sciences), and carboxylic acid modified cellulose (CMC) such as that available under the tradename KLUCEL (from Ashland). These homopolymers and copolymers have the same types of carboxylic acid side groups that can be neutralized with some alkaline chemicals to form an aqueous buffer system. These polymers are water soluble or dispersible or capable of forming a hydrogel with water solution.

Preferred poly acids are the high molecular weight polymers of acrylic acid, chemically crosslinked with polyalkenyl alcohols or divinyl glycol, available under the tradename CARBOPOL. Each primary particle can be viewed as a network structure of polymer chains interconnected by crosslinks, which results in polymers with molecular weights of up to 3 billion Daltons to 4 billion Daltons. Without the crosslinks, the primary particle would be a collection of linear polymer chains, physically intertwined but not chemically bonded. These polymers swell up to 1,000 times their original volume (and ten times their original diameter) in water to form a gel when exposed to a pH environment above their pKa of 6±0.5. The carboxylate groups on the polymer backbone ionize, resulting in repulsion between the negative particles, which adds to the swelling of the polymer. The gel contains a large amount of swollen microgel particles, with interstitial spaces in which insoluble particles can be entrapped (suspended).

CARBOPOL polymer microgels are easily moved by shear, but once the shear stops, the macro-gel structure immediately forms again. This enables highly viscous suspensions to be stirred or pumped easily, with instantaneous recovery once the stirring or pumping ceases. CARBOPOL polymers swell when hydrated and neutralized, forming a colloidal dispersion and trapping insoluble ingredients.

Suitable CARBOPOL polymers include those available as CARBOPOL 974P NF, CARBOPOL 971P NF, and CARBOPOL 71G NF polymers. Of these, CARBOPOL 974P NF polymer is particularly preferred. It is highly crosslinked and produces highly viscous gels similar to mayonnaise. Viscosity of CARBOPOL 974P NF polymer at pH 7 is 10,000 mPa*s at a concentration of 0.2%, 30,000 mPa*s at a concentration of 0.5%, 60,000 mPa*s at a concentration of 1.0%, 85,000 mPa*s at a concentration of 2.0%, measured with Brookfield viscosity at 20 revolutions per minute (rpm). The viscosities of CARBOPOL 974P NF polymer at pH 6 and pH 7 are very close.

Another suitable crosslinked poly acid is that available under the trade designation NOVEON AA-1 polycarbophil (a high molecular weight acrylic acid polymer crosslinked with divinyl glycol) from Lubrizol Advanced Materials.

Compositions of the present disclosure include at least 0.1 wt-%, or at least 0.5 wt-%, of a crosslinked poly acid having carboxylic acid side groups, based on the total weight of the aqueous composition. Compositions of the present disclosure include up to 3.0 wt-%, or up to 1.5 wt-%, of a crosslinked poly acid having carboxylic acid side groups, based on the total weight of the aqueous composition.

Multivalent Cation Salts

Suitable multivalent cation salts for use in compositions of the present disclosure include a +2 multivalent cation, a +3 multivalent cation, or a combination thereof. In certain embodiments, the multivalent cation salts include a +3 multivalent cation. Various combinations of such salts may be used if desired.

Examples of suitable multivalent cations in the salts include those selected from Ca, Mg, Ba, Mn, Fe, Zn, Al, Cu, and a combination thereof. In certain embodiments, the multivalent cation is selected from Ca, Zn, Al, and a combination thereof. In certain embodiments, the multivalent cation includes Al and Ca.

Examples of suitable counterions in the multivalent cation salts include those selected from chloride, nitrate, gluconate, lactate, acetate, and sulfate. Various combinations of counterions may be used if desired. Also, the salts may also include hydrates thereof.

In certain embodiments, the multivalent cation salts comprising calcium (i.e., calcium salts) are selected from calcium chloride, calcium nitrate, calcium gluconate, calcium lactate gluconate, calcium acetate, hydrates thereof, and combinations thereof. In certain embodiments, the multivalent cation salts comprising calcium are selected from calcium chloride, calcium nitrate, hydrates thereof, and combinations thereof.

In certain embodiments, the multivalent cation salts comprising aluminum (i.e., aluminum salts) are selected from aluminum chloride, aluminum sulfate, aluminum nitrate, potassium aluminum sulfate, their hydrates, and combinations thereof. In certain embodiments, the multivalent cation salts comprising aluminum are selected from aluminum chloride, aluminum nitrate, aluminum chloride, and combinations thereof.

Compositions of the present disclosure include at least 0.025 wt-%, at least 0.05 wt-%, or at least 0.1 wt-%, of a multivalent cation salt, based on the total weight of the aqueous composition. Compositions of the present disclosure include up to 1.75 wt-%, up to 1.5 wt-%, or up to 1.0 wt-%, of a multivalent cation salt, based on the total weight of the aqueous composition.

Active Agent—Sodium Fluoride

Aqueous oral care fluoride treatment compositions of the present disclosure include sodium fluoride as the active agent. In certain embodiments, a treatment composition includes at least 1.0 wt-%, based on the total weight of the aqueous composition. In certain embodiments, a treatment composition includes up to 2.5 wt-%, based on the total weight of the aqueous composition.

In use, the fluoride releasing composition can be applied to the oral cavity. In one embodiment, the fluoride releasing composition is typically applied directly to one or more teeth. The fluoride releasing composition is typically maintained in contact with the teeth for a sufficient time to release a therapeutically effective amount of fluoride. The release of fluoride from the fluoride releasing composition can be measured, for example, by the method described in the Examples Section of this disclosure.

In certain embodiments, a treatment composition of the present disclosure releases at least 30% (or at least 40%, or at least 50%) of the sodium fluoride in 5 minutes or less. In certain embodiments, a treatment composition of the present disclosure releases at least 50% (or at least 60%, or at least 70%) of the sodium fluoride in 10 minutes or less. In certain embodiments, a treatment composition of the present disclosure releases at least 80% (or at least 90%, or at least 95%) of the sodium fluoride in 20 minutes or less.

In certain embodiments, a treatment composition of the present disclosure releases up to 93% (or up to 90%, or up to 88%) of the sodium fluoride in 1 minute or less. In certain embodiments, a treatment composition of the present disclosure releases up to 97% (or up to 95%, or up to 94%) of the sodium fluoride in 3 minutes or less. In certain embodiments, a treatment composition of the present disclosure releases up to 99% (or up to 98%, or up to 96%) of the sodium fluoride in 5 minutes or less.

In certain embodiments, a treatment composition of the present disclosure releases 100% (or no less than 98%, or no less than 90%) of the sodium fluoride in 10 minutes or less. In certain embodiments, a treatment composition of the present disclosure releases 100% (or no less than 99%, or no less than 95%) of the sodium fluoride in 15 minutes or less.

In certain embodiments, a treatment composition of the present disclosure releases 100% (or no less than 99%, or no less than 98%) of the sodium fluoride in 20 minutes or less.

Additional Optional Active Agents

Aqueous oral care fluoride treatment compositions of the present disclosure can also contain one or more active agents in addition to sodium fluoride. When included, the one or more additional active agents usually, but not always, include one or more active agents that are active in the oral cavity against disorders, diseases, or conditions of the teeth, gums, cheeks, tongue, roof of the mouth, and the like.

Examples of additional active agents that can be employed include one or more other fluorine-containing compounds, such as sodium monofluorophosphate, stannous fluoride, calcium fluoride, strontium fluoride, zinc fluoride, zinc potassium fluoride, ammonium fluoride, potassium, magnesium fluoride, and combinations thereof.

Examples of additional active agents that can be employed include one or more whitening agents, anticalculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, and proteins. Various combinations of such additional active agents may be used if desired. When employed, one or more additional active agents will be typically used in amounts sufficient to achieve their intended effect.

When employed, the whitening agents can be a wide variety of suitable whiting agents. The whitening agents can include, for example, a peroxide whitening agent, a non-peroxide whitening agent, or both. Peroxide whitening agents include hydrogen peroxide, peroxide of alkali or alkaline earth metals, such as sodium peroxide, potassium peroxide, lithium peroxide, magnesium peroxide, calcium peroxide, barium peroxide, and the like, glyceryl hydrogen peroxide, alkyl hydrogen peroxide, dialkyl peroxide, peroxy acids or peroxy acid salts, benxoyl peroxide, urea peroxide, and the like. Hydrogen peroxide is most common. Non-peroxide whitening agents include chlorine dioxide, chlorites, and hypochlorites. Chlorites and hyperchlorites are typically in the form of alkali or alkaline earth metal salts, such as salts of lithium, potassium, sodium, magnesium, calcium, or barium. Colorants, titanium dioxide, and hydroxyapatite can also be used.

When employed, the anticalculus agents can be a wide variety of suitable anticalculus agents. The anticalculus agents can include, for example, phosphates, polyphosphates, such as pyrophosphates, polyolefin sulfonates, polyolefin phosphates, diphosphonates, phosphonoalkane carboxylic acids, and salts thereof, typically alkali metal or ammonium salts.

When employed, the remineralization agents can be a wide variety of suitable remineralization agents. The remineralization agents can include, for example, materials that release calcium ions, phosphorous-containing ions, or both, such as calcium phosphate (e.g., mono-, di-, and/or tricalcium phosphate), hydroxyapatite, calcium carbonate, and the like.

Examples of materials that release calcium ions are calcium salts that are water soluble, such as those selected from calcium chloride, calcium nitrate, calcium gluconate, calcium lactate gluconate, calcium acetate, hydrates thereof, and combinations thereof. In certain embodiments, the calcium salt is selected from calcium chloride, calcium nitrate, hydrates thereof, and combinations thereof.

A calcium salt can also be used to modulate the fluoride release profile.

When employed, the stannous sources can be a wide variety of suitable source of stannous ions. The stannous ion sources can include, for example, stannous halides, organic stannous carboxylate salts, such as stannous formate, stannous acetate, stannous gluconate, stannous lactate, stannous tartrate, and stannous citrate. When the fluoride source is stannous fluoride, it can also function as a stannous source.

When employed, the antimicrobial agents can include a wide variety of orally acceptable antimicrobial agents. Examples include triclosan, 8-hydroxyquinoline, zinc ion, stannous ion, cupric compounds, phthalic acid and salts thereof, quaternary ammonium compounds, sanguinarine, salicylanilide, salicylic acid, thymol, eugenol, neomycin, kanamycin, clindamycin, amoxicillin, tetracycline, doxycycline, minocycline, metronidazole, chlorohexidine, and the like.

When employed, the antioxidants can be a wide variety of orally acceptable antioxidants. Examples include butylated hydroxy anisone, butylated hydroxy toluene, vitamin A, carotenoids, vitamin E, flavonoids, polyphenols, ascorbic acid or salts thereof, chlorophyll, melatonin, and the like.

When employed, the saliva stimulants can be a wide variety of orally acceptable saliva stimulants. Examples include citric acid, lactic acid, succinic acid, ascorbic acid, adipic acid, fumaric acid, and tartaric acid.

When employed, the breath freshening agents can be a wide variety of orally acceptable breath freshening agents. Examples include zinc salts such as zinc salts of gluconate, citrate, and chlorite, alpha-ionone, and the like.

When employed, the antiplaque agents can be a wide variety of orally acceptable antiplaque agents. Examples include stannous salts, salts of copper, magnesium or strontium, dimethicone copolyols, such as cetyl dimethicone copolyol, papain, glucamylase, glucose oxidase, urea, calcium lactate, calcium glycerophosphate, strontium polyacrylates, and the like. Further examples of antiplaque agents include biofilm inhibition agents, particularly those described in U.S. Pat. No. 8,968,709 (Yang et al.).

When employed, the anti-inflammatory agents can be a wide variety of orally acceptable anti-inflammatory agents. Examples include steroids such as flucinolone and hydrocortisone, non-steroidal anti-inflammatory drugs such as ketorolac, flurbiprofen, ibuprofen, naproxen, indomethacin, diclofenac, etodolac, indomethacin, sulindac, tomlmetin, ketoprofen, fenoprofen, piroxicam, nabumetone, acetyl salicylic acid, salicylic acid, diflunisal, meclofenamate, mefenamic acid, oxyphenbutazone, phenylbutazone, and the like.

When employed, the $H_2$ antagonists can be a wide variety of orally acceptable $H_2$ antagonists. Examples include cimetidine, etinidine, ranitidine, tiotidine, lupitidine, denetidine, famotidine, roxatidine, pifatidine, lamtidine, zaltidine, nizatidine, mifentidine, ramixotidine, loxtidine, bisfentidine, sufotidine, ebrotidine, impromdine, and the like.

When employed, the desensitizing agents can be a wide variety of orally acceptable desensitizing agents. Examples include potassium citrate, potassium chloride, potassium tartrate potassium, bicarbonate, potassium oxalate, potassium nitrate, strontium salts, arginine, acetyl salicylic acid or salts thereof, salicylic acid or salts thereof, codeine, acetaminophen, and the like.

When employed, the nutrients can be a wide variety of orally acceptable nutrients. Examples include vitamins, such as vitamins C, D, thiamine, riboflavin, folic acid, nicotinamide, niacin, pyridoxine, bioflavonoids, and the like, supplements, such as amino acids, lipotropics, fish oil, polyunsaturated fatty acids, eicosapentanoic acid, docosahexanic acid, coenzyme Q10, ubiquinone, minerals such as potassium, and the like.

When employed, the proteins can include a wide variety of orally acceptable proteins. Examples include milk proteins, peroxide producing enzymes, amylase, papain, glucoamylase, glucose oxidase, and the like.

Buffers

Aqueous oral care fluoride treatment compositions of the present disclosure include a pharmaceutically acceptable buffer. The type and amount of such buffer is selected to provide a treatment composition with a pH of at least 6, or at least 6.5. In certain embodiments, the type and amount of such buffer is selected to provide a treatment composition with a pH of up to 8, up to 7.5, or up to 7. In certain embodiments, the type and amount of such buffer is selected to provide a treatment composition with a pH of 6.5 to 7.5, or a pH of 7.0. A wide variety of suitable pharmaceutically acceptable buffers can be included. Examples include acetate (e.g., sodium acetate), sodium carbonate, citrate (e.g., sodium citrate), tartrate, glycylglycine, histidine, glycine, lysine, arginine, sodium dihydrogen phosphate, di sodium hydrogen phosphate, sodium phosphate, tris(hydroxymethyl)-aminomethan, or mixtures thereof.

Thickeners

In certain embodiments, aqueous oral care fluoride treatment compositions of the present disclosure include a thickener to provide a composition with a suitable viscosity to allow for the desired method of application. For example, a suitable thickener in a sufficient amount may be used to achieve a solution viscosity adequate to maintain the composition in an inverted mouthpiece tray applicator for up to about four minutes (typical time for a professionally applied fluoride treatment), and yet be fluid enough to have acceptable handling characteristics for the dental operator (e.g., when dispensing into a dental tray applicator). Or, a suitable thickener in a sufficient amount may be used to achieve a solution viscosity adequate to paint on a tooth surface.

In certain embodiments, the type and amount of thickener is selected to provide a treatment composition with a viscosity of at least 0.5 Pascal seconds at a shear rate of 1.0/second. In certain embodiments, a type and amount of thickener is selected to provide a treatment composition with a viscosity of up to 500 Pascal seconds at a shear rate of 1.0/second.

In certain embodiments, a thickener is present in a treatment composition in an amount of less than 2.5 wt-%, based on the total weight of the aqueous composition. In certain embodiments, a thickener is present in an amount of at least 0.5 wt-%, based on the total weight of the aqueous composition.

Suitable thickeners are typically those that are generally safe for human ingestion (FDA approved for internal use), do not bind fluoride ions, and do not significantly affect the bioavailability of fluoride ions.

In certain embodiments, the thickener is selected from natural gums, non-acid cellulose derivatives (e.g., hydroxyethyl cellulose), inorganic fillers (e.g., colloidal silica, fumed silica, alumina, titania, and zinc oxide), alkylene oxide polymers (e.g., polyethylene glycol, polypropylene glycol, and copolymers of polyethylene glycol and polypropylene glycol), non-acid modified starches, and combinations thereof.

Optional Additives

In certain embodiments, aqueous oral care fluoride treatment compositions of the present disclosure include one or more optional additives including flavoring agents (i.e., flavorants) and sweeteners. Various combinations of such additives may be used if desired.

In certain embodiments, aqueous oral care fluoride treatment compositions of the present disclosure include a sweetener. A wide variety of orally acceptable sweeteners can be used. Common sweeteners include xylitol, sorbitol, sucralose, aspartame, saccharin, usually sodium saccharine, and the like. When present, a sweetener can be used in any suitable amount, most often in an amount sufficient to impart a pleasant sweetness to the composition. The suitable amount is typically 0.5 wt-% to 15 wt-%, based on the total weight of the aqueous composition.

In certain embodiments, aqueous oral care fluoride treatment compositions of the present disclosure include a flavoring agent. A wide variety of orally acceptable flavoring agents can be used. Common flavoring agents include peppermint oil, spearmint oil, cherry flavor, citric acid, orange flavor, vanilla, strawberry flavor, coconut flavor, and bubble gum flavor. When present, a flavoring agent can be used in any suitable amount, most often in an amount sufficient to impart a desired flavor to the composition. The suitable amount is typically 1 wt-% to 4 wt-%, based on the total weight of the aqueous composition.

EXEMPLARY EMBODIMENTS

Embodiment 1 is an aqueous oral care fluoride treatment composition comprising: 0.1 wt-% to 3.0 wt-% of a crosslinked poly acid having carboxylic acid side groups; a pharmaceutically acceptable buffer; 1.0 wt-% to 2.5 wt-% of sodium fluoride; 0.025 wt-% to 1.75 wt-% of a multivalent cation salt; and at least 60 wt-% water; wherein the weight percentages are based on the total weight of the aqueous composition.

Embodiment 2 is the treatment composition of embodiment 1 wherein the crosslinked poly acid is present in an amount of 0.5 wt-% to 1.5 wt-%.

Embodiment 3 is the treatment composition of embodiment 1 or 2 wherein the crosslinked poly acid comprises a homopolymer or a copolymer of one or more monomers having one or more carboxylic acid groups.

Embodiment 4 is the treatment composition of embodiment 3 wherein the crosslinked poly acid comprises a homopolymer or a copolymer of acrylic add, maleic acid, maleic anhydride, itaconic acid, vinyl ether, alkyl acrylates, saccharides, and a combination thereof.

Embodiment 5 is the treatment composition of embodiment 4 wherein the crosslinked poly acid comprises a homopolymer or a copolymer of acrylic acid, maleic acid, itaconic acid, (C10-C30)alkyl acrylate, and a combination thereof.

Embodiment 6 is the treatment composition of embodiment 5 wherein the crosslinked poly acid comprises a crosslinked polyacrylic acid homopolymer.

Embodiment 7 is the treatment composition of any of the previous embodiments wherein the crosslinked poly acid comprises a crosslinker selected from allyl sucrose, allyl pentaerythritol, glycerol, diglycerol, polyglycerol, polyalkenyl alcohols, divinyl glycol, and a combination thereof.

Embodiment 8 is the treatment composition of embodiment 7 wherein the polyacrylic acid is crosslinked with allyl sucrose or allyl pentaerythritol.

Embodiment 9 is the treatment composition of any of the previous embodiments wherein the crosslinked poly acid in a pH 7.5 buffer at 0.5 wt-% has a viscosity of 4,000-100,000 cP.

Embodiment 10 is the treatment composition of any of the previous embodiments wherein the multivalent cation salt comprises a +2 multivalent cation, a +3 multivalent cation, or a combination thereof.

Embodiment 11 is the treatment composition of any of the preceding embodiments wherein the multivalent cation salt comprises a multivalent cation selected from Ca, Mg, Ba, Mn, Fe, Zn, Al, Cu, and a combination thereof.

Embodiment 12 is the treatment composition of embodiment 11 wherein the multivalent cation salt comprises a multivalent cation selected from Ca, Zn, Al, and a combination thereof.

Embodiment 13 is the treatment composition of embodiment 12 wherein the multivalent cation salt comprises Al and Ca.

Embodiment 14 is the treatment composition of any of the preceding embodiments wherein the multivalent cation salt comprises a chloride salt, a nitrate salt, a gluconate salt, a lactate salt, an acetate salt, a sulfate, hydrates thereof, and combinations thereof.

Embodiment 15 is the treatment composition of any of embodiments 11 through 14 wherein the multivalent cation salt comprising calcium is selected from calcium chloride, calcium nitrate, calcium gluconate, calcium lactate gluconate, calcium acetate, hydrates thereof, and combinations thereof.

Embodiment 16(a) is the treatment composition of embodiment 15 wherein the multivalent cation salt comprising calcium is selected from calcium chloride, calcium nitrate, hydrates thereof, and combinations thereof.

Embodiment 16(b) is the treatment composition of any of embodiments 11 through 16(a) wherein the multivalent cation salt comprising aluminum is selected from aluminum chloride, aluminum sulfate, aluminum nitrate, potassium aluminum sulfate, their hydrates, and combinations thereof.

Embodiment 17 is the treatment composition of any of the preceding embodiments wherein the multivalent cation salt is present in a total amount of 0.05 wt-% to 1.5 wt-%, or 0.1 wt-% to 1.0 wt-%.

Embodiment 18 is the treatment composition of any of the preceding embodiments further comprising a thickener.

Embodiment 19 is the treatment composition of embodiment 18 wherein the thickener is present in an amount sufficient to provide the composition with a viscosity of 0.5 to 500 Pascal seconds at a shear rate of 1.0/second.

Embodiment 20 is the treatment composition of embodiment 18 or 19 wherein the thickener is present in an amount of at least 0.5 wt-%, and less than 2.5 wt-%.

Embodiment 21 is the treatment composition of any of embodiments 18 through 20 wherein the thickener is selected from natural gums, non-acid cellulose derivatives, inorganic fillers, alkylene oxide polymers, non-acid modified starches, and combinations thereof.

Embodiment 22 is the treatment composition of any of the preceding embodiments which has a pH of 6 to 8, or a pH of 6.5 to 7.5.

Embodiment 23 is the treatment composition of embodiment 22 which has a p of 6 to 7, or a pH of 7.0.

Embodiment 24 is the treatment composition of any of the preceding embodiments comprising less than 5 wt-% of an organic solvent that functions as a carrier liquid (e.g., ethanol).

Embodiment 25 is the treatment composition of any of the preceding embodiments which releases at least 30% (or at least 40%, or at least 50%) of the sodium fluoride in 5 minutes or less.

Embodiment 26 is the treatment composition of any of the preceding embodiments which releases at least 50% (or at least 60%, or at least 70%) of the sodium fluoride in 10 minutes or less.

Embodiment 27 is the treatment composition of any of the preceding embodiments which releases at least 80% (or at least 90%, or at least 95%) of the sodium fluoride in 20 minutes or less.

Embodiment 28 is the treatment composition of any of the preceding embodiments which releases up to 93% (or up to 90%, or up to 88%) of the sodium fluoride in 1 minute or less.

Embodiment 29 is the treatment composition of any of the preceding embodiments which releases up to 97% (or up to 95%, or up to 94%) of the sodium fluoride in 3 minutes or less.

Embodiment 30 is the treatment composition of any of the preceding embodiments which releases up to 99% (or up to 98%, or up to 96%) of the sodium fluoride in 5 minutes or less.

Embodiment 31 is the treatment composition of any of the preceding embodiments which releases 100% (or no less than 98%, or no less than 90%) of the sodium fluoride in 10 minutes or less.

Embodiment 32 is the treatment composition of any of the preceding embodiments which releases 100% (or no less than 99%, or no less than 95%) of the sodium fluoride in 15 minutes or less.

Embodiment 33 is the treatment composition of any of the preceding embodiments which releases 100% (or no less than 99%, or no less than 98%) of the sodium fluoride in 20 minutes or less.

Embodiment 34 is the treatment composition of any of the preceding embodiments comprising at least 70 wt-% (or at least 80 wt-%) water.

Embodiment 35 is the treatment composition of any of the preceding embodiments comprising up to 96 wt-% (or up to 90 wt-%) water.

Embodiment 36 is the treatment composition of any of the preceding embodiments comprising one or more active agents in addition to sodium fluoride.

Embodiment 37 is the treatment composition of embodiment 36 wherein the one or more active agents comprise whitening agents, anticalculus agents, remineralization agents, stannous sources, antimicrobial agents, antioxidants, saliva stimulating agents, breath freshening agents, anti-plaque agents, anti-inflammatory agents, $H_2$ antagonists, desensitizing agents, nutrients, proteins, or combinations thereof.

Embodiment 38 is the treatment composition of any of the preceding embodiments further comprising a flavoring agent.

Embodiment 39 is the treatment composition of any of the preceding embodiments further comprising a sweetener.

Embodiment 40 is a method of providing fluoride to a patient's tooth surface, the method comprising applying an aqueous oral care fluoride treatment composition of any of the preceding embodiments to the patient's tooth surface.

Embodiment 41 is the method of embodiment 40 wherein applying comprises painting the treatment composition on the patient's tooth surface.

Embodiment 42 is the method of embodiment 40 wherein applying comprises dispensing the treatment composition into a dental tray and attaching the tray having the treatment composition therein to the patient's tooth surface.

Embodiment 43 is the method of embodiment 42 wherein the dental tray comprises an orthodontic aligner treatment tray.

Embodiment 44 is a method of reducing the incidence of dental caries in a patient in need thereof, the method comprising applying an aqueous oral care fluoride treatment composition of any one of embodiments 1 through 39 to the patient's tooth surface.

Embodiment 45 is the method of embodiment 44 wherein applying comprises painting the treatment composition on the patient's tooth surface.

Embodiment 46 is the method of embodiment 44 wherein applying comprises dispensing the treatment composition into a dental tray and attaching the tray having the treatment composition therein to the patient's tooth surface.

Embodiment 47 is the method of embodiment 46 wherein the dental tray comprises an orthodontic aligner treatment tray.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

EXAMPLES

TABLE 1

Materials

| Description | Source | Location |
|---|---|---|
| CARBOPOL 974P NF polymer (USP/NF) monograph for Carbomer Homopolymer Type B; carboxypolymethylene | The Lubrizol Corporation | Wickliffe, Ohio, USA |
| Sodium hydrogen phosphate, $Na_2HPO_4$ | J. T. Baker | Center valley, PA, USA |
| Xylitol | Roquette | Keokuk, IA, USA |
| Sucralose | VWR | West Chester, PA, USA |
| Calcium chloride dehydrate, $CaCl_2 \cdot 2H_2O$ | J. T. Baker | Center valley, PA, USA |
| Zinc chloride hydrate, $ZnCl_2 \cdot H_2O$ | Alfa Aesar | Tewksbury, MA, USA |
| Aluminum chloride hexahydrate, $AlCl_3 \cdot 6H_2O$ | Alfa Aesar | Tewksbury, MA, USA |
| Strontium chloride hexahydrate, $SrCl_2 \cdot 6H_2O$ | EMD Millipore | Billerica, MA, USA |
| Iron chloride hexahydrate, $FeCl_3 \cdot 6H_2O$ | Alfa Aesar | Tewksbury, MA, USA |
| Flavor (Bubblegum) | Footee & Jenks | Camden, NJ, USA |
| NATROSOL 250HHX Pharm, hydroxy ethyl cellulose (HEC) | Ashland | Wilmington, DE, USA |
| Sodium fluoride, NaF | Sunlit Fluo & Chemical Co. | Taipei, Taiwan |
| Triethanolamine | J. T. Baker | Center Valley, PA | pH Testing pH testing was carried out on a standard pH meter after calibration. The pH meter was ACCUMET model 15 pH meter from Fisher Scientific. The measurement was performed by inserting the pH probe into the solution, waiting for 2 minutes and recording the pH value. pH values were listed in the example table.

Fluoride Release Test

Fluoride release was measured on a Mettler Toledo T70 titrator. The Cole Parmer fluoride electrode was first calibrated with parts per million (ppm) fluoride standards with TISAB III before measuring samples for fluoride release each day (Total Ionic Strength Adjustment Buffer (TISAB) III concentrate solution is for use with fluoride ion selective electrodes, Sigma Aldrich). Each Example composition was coated in a thin layer on RINZL Plastic microscope slide with 2.54 centimeters' square area for both sides of the slide. The total weight of coating was about 0.045 gram. The fluoride meter titrator cup was filled with 50 milliliters of a mixture of 45 mL of MilliQ DI water and 5 mL TISAB III concentrate. The fluoride ion selective electrode was placed in the titrator cup of diluted TISAB III solution and allowed to equilibrate the meter for 30 seconds before analyzing each sample. After 30 seconds, the clamped sample was lowered into the 50 milliliters of diluted TISAB III solution. Fluoride release (mV) was measured at different time points during a 30-minute titration with Mettler Toledo T70 titrator. The fluoride release was calculated against the fluoride standards calibration curve. The average of two titrations for each example was reported.

Preparation of Buffered CARBOPOL Polyacid Solutions

Alkaline chemicals, such as disodium hydrogen phosphate, triethanolamine, were first dissolved in deionized (DI) water in a glass jar to form clear solutions. Then CARBOPOL 974P NF was added into the glass jar, which was roller mixed to form solutions which were slightly viscous and slightly hazy. The pH was measured with a standard pH meter. Four different buffered CARBOPOL solutions (BCS) were prepared with the following formulations shown in Table 2.

TABLE 2

Buffered CARBOPOL Solutions

| COMPONENT | BCS-1 | BCS-2 | BCS-3 | BCS-4 |
|---|---|---|---|---|
| DI Water | 773 | 770 | 774 | 776 |
| CARBOPOL 974PNF | 8 | 8 | 8 | 8 |
| Triethanolamine | 0 | 0 | 8 | 8 |
| $Na_2HPO_4$ | 19 | 22 | 10 | 8 |
| Total (parts) | 800 | 800 | 800 | 800 |
| pH | 6.45 | 6.52 | 6.75 | 6.63 |

Example Preparation Procedure

Appropriate amounts of the Buffered CARBOPOL polyacid solutions were added to a plastic bottle; then calculated amounts of sodium fluoride, xylitol, flavor/sweetener were added into the plastic bottle with magnetic stirring for 30 minutes to dissolve all these chemicals into aqueous example solutions. Multivalent cation salts were first dissolved in DI water in a separate glass jar, then these salt solutions were added slowly into the CARBOPOL solution in the plastic bottle. The mixture was mixed with magnetic stirring for 1 hour. Then hydroxyl ethyl cellulose (HEC) was added into the example solutions which were mixed for another 30 minutes with magnetic stirring. Finally, the example compositions were additionally mixed on a roller mixer for 1-2 days to form viscous aqueous coating liquid. The total amount of each example is shown in Tables 3A-3E, with amounts in grams.

TABLE 3A

EXAMPLES Ex. 1-Ex. 5 and Comparative Example CE. 1

| COMPONENT | Ex. 1 | Ex. 2 | Ex. 3 | Ex. 4 | Ex. 5 | CE. 1 |
|---|---|---|---|---|---|---|
| CARBOPOL 974P NF | 0.8 | 0.8 | 0.8 | 0.8 | 0.8 | 0.8 |
| Water to dissolve CARBOPOL | 77.3 | 77.3 | 77.3 | 77.3 | 77.3 | 77.3 |
| $Na_2HPO_4$ | 1.9 | 1.9 | 1.9 | 1.9 | 1.9 | 1.9 |
| Triethanolamine | 0 | 0 | 0 | 0 | 0 | 0 |
| NaF | 2 | 2 | 2 | 2 | 2 | 2 |
| Flavor | 0 | 0 | 2 | 2 | 2 | 2 |
| Xylitol | 5 | 5 | 5 | 5 | 5 | 5 |
| Sucralose | 0 | 0 | 0.4 | 0 | 0 | 0.4 |
| HEC | 1.2 | 1.2 | 1.2 | 1.2 | 1.2 | 1.2 |
| Water to dissolve salt | 11.4 | 11.4 | 8.6 | 9.1 | 9.4 | 9.4 |
| $SrCl_2 \cdot 6H_2O$ | 0.2 | 0 | 0 | 0 | 0 | 0 |
| $ZnCl_2 \cdot H_2O$ | 0 | 0 | 0 | 0 | 0 | 0 |
| $FeCl_3 \cdot 6H_2O$ | 0 | 0.2 | 0 | 0 | 0 | 0 |
| $AlCl_3 \cdot 6H_2O$ | 0 | 0 | 0 | 0.4 | 0.4 | 0 |
| $CaCl_2 \cdot 2H_2O$ | 0.2 | 0.2 | 0.8 | 0.3 | 0 | 0 |
| Total water | 88.7 | 88.7 | 85.9 | 86.4 | 86.7 | 86.7 |
| Total | 100 | 100 | 100 | 100 | 100 | 100 |
| pH | 6.15 | 6.05 | 6.11 | 6.16 | 6.19 | 6.22 |

TABLE 3B

EXAMPLES Ex-6-Ex-10 and Comparative Example CE-2

| COMPONENT | Ex. 6 | Ex. 7 | Ex. 8 | Ex. 9 | Ex. 10 | CE. 2 |
|---|---|---|---|---|---|---|
| CARBOPOL 974P NF | 0.8 | 0.8 | 0.8 | 0.8 | 0.8 | 0.8 |
| Water to dissolve CARBOPOL | 77 | 77 | 77 | 77 | 77 | 77 |
| $Na_2HPO_4$ | 2.2 | 2.2 | 2.2 | 2.2 | 2.2 | 2.2 |
| Triethanolamine | 0 | 0 | 0 | 0 | 0 | 0 |
| NaF | 2 | 2 | 2 | 2 | 2 | 2 |
| Flavor | 2 | 2 | 2 | 2 | 2 | 2 |
| Xylitol | 5 | 5 | 5 | 5 | 5 | 5 |
| Sucralose | 0 | 0 | 0 | 0 | 0 | 0 |
| HEC | 1.2 | 1.2 | 1.2 | 1.2 | 1.2 | 1.2 |
| Water to dissolve salt | 9.2 | 9.1 | 9.3 | 9.1 | 9.2 | 9.8 |
| $SrCl_2 \cdot 6H_2O$ | 0 | 0 | 0 | 0 | 0 | 0 |
| $ZnCl_2 \cdot H_2O$ | 0.2 | 0.2 | 0 | 0.15 | 0.1 | 0 |
| $FeCl_3 \cdot 6H_2O$ | 0 | 0 | 0 | 0 | 0 | 0 |
| $AlCl_3 \cdot 6H_2O$ | 0 | 0 | 0 | 0.15 | 0.1 | 0 |
| $CaCl_2 \cdot 2H_2O$ | 0.4 | 0.5 | 0.5 | 0.4 | 0.4 | 0 |
| Total water | 86.2 | 86.1 | 86.3 | 86.1 | 86.2 | 86.8 |
| Total | 100 | 100 | 100 | 100 | 100 | 100 |
| pH | 6.08 | 6.05 | 6.29 | 6.18 | 6.27 | 6.38 |

TABLE 3C

EXAMPLES Ex-11-Ex-17

| COMPONENT | Ex. 11 | Ex. 12 | Ex. 13 | Ex. 14 | Ex. 15 | Ex. 16 | Ex. 17 |
|---|---|---|---|---|---|---|---|
| CARBOPOL 974P NF | 0.8 | 0.8 | 0.8 | 0.8 | 0.8 | 0.8 | 0.8 |
| Water to dissolve CARBOPOL | 77.4 | 77.4 | 77.4 | 77.6 | 77.6 | 77.6 | 77.6 |
| $Na_2HPO_4$ | 1 | 1 | 1 | 0.8 | 0.8 | 0.8 | 0.8 |
| Triethanolamine | 0.8 | 0.8 | 0.8 | 0.8 | 0.8 | 0.8 | 0.8 |
| NaF | 2 | 2 | 2 | 2 | 2 | 2 | 2 |
| Flavor | 2 | 2 | 2 | 2 | 2 | 2 | 2 |
| Xylitol | 5 | 5 | 5 | 5 | 5 | 5 | 5 |
| Sucralose | 0 | 0 | 0 | 0 | 0 | 0 | 0 |
| HEC | 1.2 | 1.2 | 1.2 | 1 | 1 | 1 | 1 |
| Water to dissolve salt | 9.2 | 9.1 | 9.4 | 9.4 | 9.5 | 9.55 | 9.45 |
| $SrCl_2 \cdot 6H_2O$ | 0 | 0 | 0 | 0 | 0 | 0 | 0 |
| $ZnCl_2 \cdot H_2O$ | 0.1 | 0.15 | 0 | 0.1 | 0 | 0 | 0 |
| $FeCl_3 \cdot 6H_2O$ | 0 | 0 | 0 | 0 | 0 | 0 | 0 |
| $AlCl_3 \cdot 6H_2O$ | 0.1 | 0.15 | 0 | 0.1 | 0.1 | 0.05 | 0.15 |

TABLE 3C-continued

EXAMPLES Ex-11-Ex-17

| COMPONENT | Ex. 11 | Ex. 12 | Ex. 13 | Ex. 14 | Ex. 15 | Ex. 16 | Ex. 17 |
|---|---|---|---|---|---|---|---|
| $CaCl_2 \cdot 2H_2O$ | 0.4 | 0.4 | 0.4 | 0.4 | 0.4 | 0.4 | 0.4 |
| Total water | 86.60 | 86.50 | 86.80 | 87.00 | 87.10 | 87.15 | 87.05 |
| Total | 100 | 100 | 100 | 100 | 100 | 100 | 100 |
| pH | 6.27 | 6.12 | 6.39 | 6.08 | 6.21 | 6.23 | 6.23 |

TABLE 3D

EXAMPLES Ex. 18-Ex. 23

| COMPONENT | Ex. 18 | Ex. 19 | Ex. 20 | Ex. 21 | Ex. 22 | Ex. 23 |
|---|---|---|---|---|---|---|
| CARBOPOL 974P NF | 0.8 | 0.8 | 0.8 | 0.8 | 0.8 | 0.8 |
| Water to dissolve CARBOPOL | 77.6 | 77.6 | 77.6 | 77.6 | 77.6 | 77.6 |
| $Na_2HPO_4$ | 0.8 | 0.8 | 0.8 | 0.8 | 0.8 | 0.8 |
| Triethanolamine | 0.8 | 0.8 | 0.8 | 0.8 | 0.8 | 0.8 |
| NaF | 2 | 2 | 2 | 2 | 2 | 2 |
| Flavor | 2 | 2 | 2 | 2 | 2 | 2 |
| Xylitol | 5 | 5 | 5 | 5 | 5 | 5 |
| Sucralose | 0.4 | 0.4 | 0.4 | 0.4 | 0.4 | 0.4 |
| HEC | 1.1 | 1.1 | 1.1 | 1.1 | 1.1 | 1.1 |
| Water to dissolve salt | 8 | 9.4 | 9.2 | 8.9 | 9.2 | 9.1 |
| $SrCl_2 \cdot 6H_2O$ | 0 | 0 | 0 | 0 | 0 | 0 |
| $ZnCl_2 \cdot H_2O$ | 0 | 0 | 0 | 0 | 0 | 0 |
| $FeCl_3 \cdot 6H_2O$ | 0 | 0 | 0 | 0 | 0 | 0 |
| $AlCl_3 \cdot 6H_2O$ | 1.5 | 0.1 | 0.3 | 0.6 | 0.2 | 0.3 |
| $CaCl_2 \cdot 2H_2O$ | 0 | 0 | 0 | 0 | 0.1 | 0.1 |
| Total water | 85.6 | 87 | 86.8 | 86.5 | 86.8 | 86.7 |
| Total | 100 | 100 | 100 | 100 | 100 | 100 |

TABLE 3E

EXAMPLES Ex. 24-Ex. 29

| COMPONENT | Ex. 24 | Ex. 25 | Ex. 26 | Ex. 27 | Ex. 28 | Ex. 29 |
|---|---|---|---|---|---|---|
| CARBOPOL 974P NF | 0.8 | 0.8 | 0.8 | 0.8 | 0.8 | 0.8 |
| Water to dissolve CARBOPOL | 77.6 | 77.6 | 77.6 | 77.6 | 77.6 | 77.6 |
| $Na_2HPO_4$ | 0.8 | 0.8 | 0.8 | 0.8 | 0.8 | 0.8 |
| Triethanolamine | 0.8 | 0.8 | 0.8 | 0.8 | 0.8 | 0.8 |
| NaF | 2 | 2 | 2 | 2 | 2 | 2 |
| Flavor | 2 | 2 | 2 | 2 | 2 | 2 |
| Xylitol | 5 | 5 | 5 | 5 | 5 | 5 |
| Sucralose | 0.4 | 0.4 | 0.4 | 0.4 | 0.4 | 0.4 |
| HEC | 0.4 | 0.7 | 1.1 | 1.5 | 1.9 | 2.3 |
| Water to dissolve salt | 9.8 | 9.5 | 9.1 | 8.7 | 8.3 | 7.9 |
| $SrCl_2 \cdot 6H_2O$ | 0 | 0 | 0 | 0 | 0 | 0 |
| $ZnCl_2 \cdot H_2O$ | 0 | 0 | 0 | 0 | 0 | 0 |
| $FeCl_3 \cdot 6H_2O$ | 0 | 0 | 0 | 0 | 0 | 0 |
| $AlCl_3 \cdot 6H_2O$ | 0.3 | 0.3 | 0.3 | 0.3 | 0.3 | 0.3 |
| $CaCl_2 \cdot 2H_2O$ | 0.1 | 0.1 | 0.1 | 0.1 | 0.1 | 0.1 |
| Total water | 87.4 | 87.1 | 86.7 | 86.3 | 85.9 | 85.5 |
| Total | 100 | 100 | 100 | 100 | 100 | 100 |
| Viscosity (pa * s) | 8.7 | 24.2 | 65.4 | 117.6 | 214.4 | 282.1 |

TABLE 4A

Fluoride Release Testing Results for EXAMPLES Ex. 1-Ex. 5, CE1

| Release time min | Ex1 % fluoride | Ex2 % fluoride | Ex3 % fluoride | Ex4 % fluoride | EX5 % fluoride | CE1 % fluoride |
|---|---|---|---|---|---|---|
| 0.0 | 2.1 | 2.1 | 1.6 | 1.6 | 1.6 | 2.1 |
| 1.0 | 90 | 87 | 78 | 73 | 80 | 97 |
| 1.5 | 93 | 91 | 81 | 76 | 82 | 98 |
| 2.0 | 94 | 93 | 83 | 78 | 82 | 99 |
| 2.5 | 96 | 95 | 85 | 79 | 83 | 100 |
| 3.0 | 97 | 96 | 88 | 80 | 83 | 100 |

TABLE 4A-continued

Fluoride Release Testing Results for EXAMPLES Ex. 1-Ex. 5, CE1

| Release time min | Ex1 % fluoride | Ex2 % fluoride | Ex3 % fluoride | Ex4 % fluoride | EX5 % fluoride | CE1 % fluoride |
|---|---|---|---|---|---|---|
| 3.5 | 97 | 97 | 89 | 81 | 83 | 100 |
| 4.0 | 98 | 98 | 91 | 82 | 84 | 100 |
| 4.5 | 98 | 98 | 92 | 83 | 85 | 100 |
| 5.0 | 99 | 98 | 93 | 83 | 85 | 100 |
| 6.0 | 99 | 99 | 95 | 84 | 86 | 100 |
| 7.0 | 99 | 99 | 97 | 86 | 88 | 100 |
| 9.0 | 99 | 99 | 98 | 88 | 91 | 100 |
| 10.0 | 99 | 100 | 99 | 90 | 92 | 100 |
| 12.0 | 99 | 100 | 99 | 92 | 94 | 100 |
| 15.0 | 100 | 100 | 100 | 95 | 97 | 100 |
| 20.0 | 100 | 100 | 100 | 98 | 99 | 100 |
| 25.0 | 100 | 100 | 100 | 99 | 100 | 100 |
| 30.0 | 100 | 100 | 100 | 100 | 100 | 100 |

TABLE 4B

Fluoride Release Testing Results for EXAMPLES Ex. 6-Ex. 10, CE2

| Release time min | Ex6 % fluoride | Ex7 % fluoride | Ex8 % fluoride | Ex9 % fluoride | EX10 % fluoride | CE2 % fluoride |
|---|---|---|---|---|---|---|
| 0.0 | 1.2 | 1.1 | 1.1 | 1.2 | 1.4 | 1.1 |
| 1.0 | 84 | 85 | 85 | 82 | 81 | 94 |
| 1.5 | 88 | 88 | 88 | 84 | 85 | 97 |
| 2.0 | 90 | 90 | 90 | 86 | 86 | 98 |
| 2.5 | 92 | 92 | 91 | 88 | 88 | 99 |
| 3.0 | 92 | 93 | 93 | 89 | 89 | 99 |
| 3.5 | 94 | 94 | 94 | 90 | 90 | 100 |
| 4.0 | 94 | 95 | 95 | 91 | 91 | 100 |
| 4.5 | 95 | 96 | 96 | 92 | 92 | 100 |
| 5.0 | 96 | 96 | 96 | 92 | 93 | 100 |
| 5.5 | 96 | 97 | 97 | 93 | 93 | 100 |
| 6.0 | 97 | 97 | 97 | 93 | 94 | 100 |
| 7.0 | 97 | 98 | 98 | 94 | 95 | 100 |
| 9.0 | 98 | 99 | 99 | 96 | 96 | 100 |
| 10.0 | 98 | 99 | 99 | 96 | 97 | 100 |
| 12.0 | 99 | 99 | 100 | 97 | 98 | 100 |
| 15.0 | 100 | 100 | 100 | 98 | 98 | 100 |
| 20.0 | 100 | 100 | 100 | 99 | 99 | 100 |
| 25.0 | 100 | 100 | 100 | 100 | 100 | 100 |
| 30.0 | 100 | 100 | 100 | 100 | 100 | 100 |

TABLE 4C

Fluoride Release Testing Results for EXAMPLES Ex. 11-Ex. 17

| Release time min | EX11 % fluoride | Ex12 % fluoride | EX13 % fluoride | EX14 % fluoride | Ex15 % fluoride | EX16 % fluoride | Ex17 % fluoride |
|---|---|---|---|---|---|---|---|
| 0.0 | 1.0 | 1.4 | 1.1 | 1.0 | 1.0 | 1.1 | 1.1 |
| 1.0 | 81 | 82 | 86 | 81 | 82 | 84 | 81 |
| 1.5 | 85 | 85 | 89 | 85 | 84 | 87 | 83 |
| 2.0 | 87 | 87 | 91 | 88 | 87 | 88 | 85 |
| 2.5 | 89 | 88 | 92 | 90 | 88 | 90 | 86 |
| 3.0 | 90 | 90 | 94 | 91 | 89 | 91 | 88 |
| 3.5 | 91 | 90 | 95 | 92 | 91 | 92 | 89 |
| 4.0 | 92 | 91 | 96 | 93 | 92 | 93 | 90 |
| 4.5 | 93 | 92 | 96 | 93 | 93 | 94 | 91 |
| 5.0 | 94 | 92 | 97 | 94 | 93 | 95 | 92 |
| 6.0 | 94 | 93 | 98 | 95 | 95 | 96 | 93 |
| 7.0 | 95 | 94 | 98 | 95 | 95 | 97 | 94 |
| 9.0 | 96 | 95 | 99 | 96 | 97 | 98 | 96 |
| 10.0 | 97 | 96 | 100 | 97 | 97 | 98 | 96 |
| 12.0 | 97 | 96 | 100 | 98 | 98 | 99 | 97 |
| 15.0 | 98 | 98 | 100 | 99 | 99 | 99 | 98 |
| 20.0 | 99 | 99 | 100 | 100 | 99 | 100 | 100 |
| 25.0 | 100 | 100 | 100 | 100 | 100 | 100 | 100 |
| 30.0 | 100 | 100 | 100 | 100 | 100 | 100 | 100 |

TABLE 4D

Fluoride Release Testing Results for EXAMPLES Ex. 18-Ex. 23

| Release time min | EX18 % fluoride | Ex19 % fluoride | Ex20 % fluoride | Ex21 % fluoride | Ex22 % fluoride | Ex23 % fluoride |
|---|---|---|---|---|---|---|
| 0.0 | 1.8 | 1.3 | 1.1 | 1.2 | 1.1 | 1.1 |
| 1.0 | 32 | 93 | 83 | 71 | 86 | 80 |
| 1.5 | 33 | 94 | 85 | 74 | 88 | 83 |
| 2.0 | 34 | 95 | 86 | 75 | 89 | 84 |
| 2.5 | 35 | 95 | 86 | 75 | 89 | 85 |
| 3.0 | 35 | 95 | 87 | 75 | 90 | 86 |
| 3.5 | 36 | 95 | 87 | 76 | 90 | 86 |
| 4.0 | 37 | 95 | 87 | 76 | 91 | 86 |
| 4.5 | 37 | 95 | 88 | 77 | 91 | 87 |
| 5.0 | 38 | 96 | 88 | 77 | 91 | 87 |
| 6.0 | 40 | 96 | 89 | 78 | 92 | 88 |
| 7.0 | 43 | 96 | 89 | 79 | 92 | 89 |
| 9.0 | 49 | 97 | 91 | 81 | 94 | 90 |
| 10.0 | 52 | 97 | 92 | 83 | 94 | 91 |
| 12.0 | 59 | 98 | 93 | 85 | 95 | 92 |
| 15.0 | 69 | 99 | 96 | 89 | 97 | 94 |
| 20.0 | 83 | 99 | 98 | 94 | 98 | 97 |
| 25.0 | 93 | 100 | 99 | 98 | 99 | 99 |
| 30.0 | 100 | 100 | 100 | 100 | 100 | 100 |

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:
1. An aqueous oral care fluoride treatment composition comprising:
   0.1 wt-% to 3.0 wt-% of a crosslinked poly acid having carboxylic acid side groups;
   a pharmaceutically acceptable buffer;
   1.0 wt-% to 2.5 wt-% of sodium fluoride;
   0.025 wt-% to 1.75 wt-% of a multivalent cation salt or hydrate thereof comprising:
     a multivalent cation selected from Ca, Al, and a combination thereof; and
     a counterion selected from chloride, nitrate, gluconate, lactate, acetate, sulfate, and combinations thereof;
   at least 60 wt-% water; and
   a thickener present in an amount sufficient to provide the composition with a viscosity of 0.5 to 500 Pascal seconds at a shear rate of 1.0/second; wherein the thickener is selected from non-acid cellulose derivatives, inorganic fillers, alkylene oxide polymers, non-acid modified starches, and combinations thereof;

wherein the weight percentages are based on the total weight of the aqueous composition; and wherein the treatment composition releases at least 30% of the sodium fluoride in 5 minutes or less.

2. The treatment composition of claim 1, wherein the crosslinked poly acid is present in an amount of 0.5 wt-% to 1.5 wt-%.

3. The treatment composition of claim 1, wherein the crosslinked poly acid comprises a homopolymer or a copolymer of one or more monomers having one or more carboxylic acid groups.

4. The treatment composition of claim 3, wherein the crosslinked poly acid comprises a homopolymer or a copolymer of acrylic acid, maleic acid, maleic anhydride, itaconic acid, vinyl ether, alkyl acrylates, saccharides, and a combination thereof.

5. The treatment composition of claim 4, wherein the crosslinked poly acid comprises a homopolymer or a copolymer of acrylic acid, maleic acid, itaconic acid, (C10-C30) alkyl acrylate, and a combination thereof.

6. The treatment composition of claim 1, wherein the multivalent cation salt comprises a +2 multivalent cation, a +3 multivalent cation, or a combination thereof.

7. The treatment composition of claim 6, wherein the multivalent cation salt comprises a +3 multivalent cation.

8. The treatment composition of claim 1, wherein the multivalent cation salt comprising calcium is selected from calcium chloride, calcium nitrate, calcium gluconate, calcium lactate gluconate, calcium acetate, hydrates thereof, and combinations thereof.

9. The treatment composition of claim 1, wherein the multivalent cation salt comprising aluminum is selected from aluminum chloride, aluminum sulfate, aluminum nitrate, potassium aluminum sulfate, their hydrates, and combinations thereof.

10. The treatment composition of claim 1, which releases up to 93% of the sodium fluoride in 1 minute or less.

11. The treatment composition of claim 1, wherein the multivalent cation salt is present in a total amount of 0.05 wt-% to 1.5 wt-%.

12. The treatment composition of claim 1, thickener is present in an amount of at least 0.5 wt-%.

13. The treatment composition of claim 12, wherein the thickener is present in an amount of less than 2.5 wt-%.

14. The treatment composition of claim 1, which has a pH of 6 to 8.

15. The treatment composition of claim 1, comprising less than 5 wt-% organic solvent.

16. The treatment composition of claim 1, comprising up to 96 wt-% water.

17. A method of providing fluoride to a patient's tooth surface, the method comprising applying an aqueous oral care fluoride treatment composition of claim 1 to the patient's tooth surface.

18. The method of claim 17, wherein applying comprises painting the treatment composition on the patient's tooth surface.

19. The method of claim 17, wherein applying comprises dispensing the treatment composition into a dental tray and attaching the tray having the treatment composition therein to the patient's tooth surface.

20. A method of reducing the incidence of dental caries in a patient in need thereof, the method comprising applying an aqueous oral care fluoride treatment composition of claim 1 to the patient's tooth surface.

21. The treatment composition of claim 1, wherein the thickener is selected from non-acid cellulose derivatives.

22. The treatment composition of claim 1, which releases no less than 98% of the sodium fluoride in 20 minutes or less.

* * * * *